(12) United States Patent
Broadley et al.

(10) Patent No.: US 7,360,442 B2
(45) Date of Patent: Apr. 22, 2008

(54) METHOD FOR MEASURING AND CALCULATING TENSILE ELONGATION OF DUCTILE METALS

(75) Inventors: Mark W. Broadley, Dowingtown, PA (US); John Eckert, Boyertown, PA (US)

(73) Assignee: Accellent, Inc., Collegeville, PA (US)

( * ) Notice: Subject to any disclaimer, the term of this patent is extended or adjusted under 35 U.S.C. 154(b) by 280 days.

(21) Appl. No.: 11/321,826

(22) Filed: Dec. 29, 2005

(65) Prior Publication Data

US 2007/0151359 A1   Jul. 5, 2007

(51) Int. Cl.
   *G01N 3/08* (2006.01)
(52) U.S. Cl. .......................................... 73/826; 702/42
(58) Field of Classification Search ................. 73/788, 73/790, 796, 799, 810, 821, 826, 830, 831, 73/834, 846; 702/43, 42, 97, 157, 158
   See application file for complete search history.

(56) References Cited

OTHER PUBLICATIONS

ASTM International: *Standard Testing Methods for Tension Testing of Metallic Materials*—Designation: E8-04—(p. 64-87).

ASTM International: *Standard Test Methods and Definitions for Mechanical Testing of Steel Products*—Designation: A370-05—(pp. 242-287).

*Primary Examiner*—Edward Lefkowitz
*Assistant Examiner*—Punam Patel
(74) *Attorney, Agent, or Firm*—Drinker Biddle & Reath LLP

(57) ABSTRACT

The present invention is a method for measuring and calculating tensile elongation of ductile metals on small diameter specimens. The method includes marking a tensile specimen with a pattern of gage markings at predetermined intervals. The tensile specimen is pulled to failure and then fitted together at the fracture. Distances between corresponding markings straddling the fracture are measured extending progressively outward from the fracture. From the measurements, elongation as a function of gage length is determined. End point elongation values (i.e., elongation at zero or near zero and infinite or very long gage lengths) are also determined. Determined elongations are scaled to reflect the values that would have been generated on a standard 0.5 inch diameter specimen. Based on the scaled elongation as a function of gage length and the end point elongation values, a value of elongation can be determined that represents a material property for FEA modeling the plastic strain behavior of a device.

20 Claims, 4 Drawing Sheets

METHOD FOR MEASURING AND CALCULATING TENSILE ELONGATION OF DUCTILE METALS

FIELD OF THE INVENTION

The present invention relates generally to tensile elongation of ductile metals, and particularly to a method for measuring and calculating tensile elongation on small diameter specimens for use as a material property for finite element analysis ("FEA") modeling the plastic strain behavior of a device.

BACKGROUND OF THE INVENTION

In the United States, tensile testing is generally performed in accordance with the procedures defined in ASTM E8 "Standard Test Methods for Tension Testing of Metallic Materials" and ASTM A370 "Standard Test Methods for Tension Testing of Steel Products". Under those test methods, Percent Elongation=((Final gage length minus Original gage length) divided by Original gage length) times 100, where Original gage length is the length between gage markings on the tensile specimen before testing and Final gage length is the length between the same gage markings after testing.

The standard tensile specimen diameter is nominally 0.5 inch. A 2-inch gage length is generally used for round, solid or tubular standard size tensile specimens. Gage length is generally understood to mean the length of the marked region on the tensile specimen over which elongation is calculated. As used herein, the term gage length will refer to the original gage length unless stated otherwise. When smaller diameter solid or tubular specimens are tensile tested to determine the material's mechanical properties, the elongation measured using the standard 2-inch gage length decreases with decreasing specimen diameter. This result is termed the "specimen size effect" on elongation. The specimen size effect is observed even when the large and small diameter specimens are taken from the same bar of raw material. There are several potential causes that need to be considered for the specimen size effect on elongation.

One potential cause is the relative size of defects present on the surface of a specimen. For ductile materials that are not notch sensitive, isolated notches less than about 5% of the specimen section (diameter for solid specimens, wall thickness for tubular specimens), do not produce an appreciable reduction in observed tensile elongation. However, for larger defects, representing a significant portion of the specimen section (i.e., greater than about 5%) localized strain (strain is generally understood to be an expression of deformation caused by the action of stress on a physical body) is increased at the defects. The result is premature fracture at the defects and lower measured tensile elongation of the overall specimen. On specimens with sections larger than about 0.010 inch, defects representing 5% or more of the specimen section can be controlled by careful sample preparation.

A second potential cause is the relation between grain size and the specimen section. As the specimen section approaches the material grain size, dislocation motion is not readily accommodated by grains with less favorable crystallographic orientations. The results are premature fracturing at grain boundaries (i.e., the zone formed at the junction of individual crystals in a polycrystalline material) of the unfavorably oriented grains and low measured elongation. The premature fracturing can be significantly improved by preparing a specimen having at least three different grains across the specimen section. For the fine grained microstructures required for small medical devices, this effect is not significant for section sizes greater than about 0.010 inch.

A third potential cause is the decrease in the proportion of necking elongation to the total elongation to failure as the specimen diameter is reduced. This effect is believed to be the predominant cause of low measured elongation for solid or tubular tensile specimen with diameters from about ⅜ inch down to about 0.020 inch when measured with a constant gage length.

The current approach to reduce the specimen size effect on measured elongation is to use a proportional gage length that varies with the specimen diameter or area. ASTM specifications allow a proportional gage length of 4 times the specimen diameter for round specimens less than 0.5 inch diameter. ISO standards specify a proportional gage length of 5.65 times the square root of the specimen cross sectional area for small diameter specimens. This is equivalent to 5 times the diameter for round, solid specimens. These proportional gage length correction factors are intended to maintain the ratio between diameter and gage length found on the standard 0.5 inch diameter specimen with a 2 inch gage length on specimens with smaller diameter. They produce an elongation value similar to the standard 0.5 inch specimen, but are difficult to implement in the testing laboratory due to the non-standard gage lengths that are required.

In addition, because of the many dimensional and proportional gage lengths recommended by industry, national and international specifications, the various measured elongations for a particular alloy and condition cannot be readily compared to each other or evaluated versus specification requirements written for a different gage length. Tables have been created by ASTM and ISO to allow conversion of elongation values for specific materials and specific gage lengths. These tables are limited to the most common alloys and gage lengths.

If the measured elongation for a given material varies with the choice of gage length, the resulting elongation values cannot be claimed to be a material property. This has not been a major issue historically because the great majority of engineered structures have been designed to withstand stresses no greater than the material's yield strength. As a result, device performance has been determined predominately by the material's elastic properties and elongation has been used only as a relative measure of the material's resistance to catastrophic failure.

Recently, medical devices called arterial stents have been designed to deform plastically during balloon expansion and take a permanent set once expanded within the artery. During the design process, the material's plastic properties, including elongation, are required to determine at what point the stent will fail in the plastic strain environment experienced during balloon expansion.

Tubing used to fabricate tubular stents is smaller than 0.250 inch and typically smaller than 0.125 inch diameter, considerably less than the 0.5 inch standard specimen diameter. This tubing is tensile tested at its finished size and material condition to determine the arterial stent material properties.

The problem currently facing device designers who wish to FEA model the plastic stain behavior of a device such as an arterial stent is the uncertainty as to which elongation value (derived from various gage lengths) should be used as a material property to accurately model the device behavior. Once the choice is made, there is still uncertainty regarding how the elongation value should be used since it includes two undifferentiated components (uniform and necking elongation) which have significantly different implications concerning the resistance of the device to tensile failure.

Elongation differentiated into its uniform and necking components, may allow optimization by the material manufacturer of one or the other component to improve device performance.

As a result, there is a need for a method of measuring and calculating elongation on small diameter solid or tubular specimens that that is unaffected by the specimen size effect, that uses a universally applicable gage length marking technique, that produces elongation values at any gage length to allow comparisons with published data and specifications using alternate gage lengths, and that differentiates between uniform and necking elongation. For continuity with current published data and specifications, the method should be capable of producing elongation values similar to those obtained on the standard 0.5 inch diameter specimen at the 2 inch gage length. From the method, an elongation value could be calculated that is representative of the tested material's plastic deformation properties independent of gage length and specimen size.

BRIEF DESCRIPTION OF THE DRAWINGS

For the purpose of illustrating the invention there are shown in the drawings various forms which are presently preferred; it being understood, however, that this invention is not limited to the precise arrangements and instrumentalities particularly shown.

SUMMARY OF THE INVENTION

Figure 1:
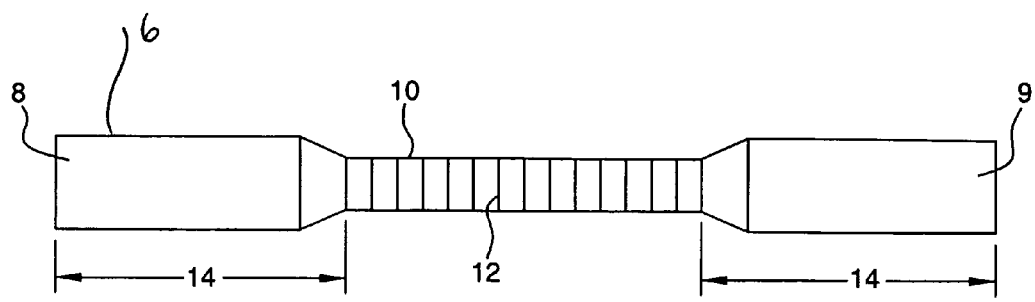
FIG. 1 is a plan view of a solid, round, smooth (unnotched) tensile specimen before tensile testing.

The present invention includes a method for measuring and calculating elongation to failure of a solid or tubular, smooth tensile specimen. The method includes fabricating the tensile specimen and marking the tensile specimen with a pattern of markings at predetermined intervals. The tensile specimen is then tested by pulling it to failure.

After testing, the specimen is characterized by two gripped regions, two end effect regions adjacent to the gripped regions with reduced elongation, at least one uniformly elongated region, a necked region, a fracture at least partially between two markings, a fracture zone including the entire fracture, and a minimum diameter.

The specimen is fitted together at the fracture. The distance between each corresponding pair of gage markings extending progressively outward from the fracture is then measured. In addition, the location of each gage marking, the minimum diameter, and the fracture are also measured. The diameter of the tensile specimen is measured at each of the gage markings, at the minimum diameter, and at the fracture.

The distances, locations and diameters from the gripped regions and the end effect regions are discarded.

Local elongation as a function of location is determined using the remaining distance (or alternatively, the diameter), and location measurements. End point elongation values (i.e., elongation at zero or near zero and elongation at infinite or distant locations) are determined. The percent reduction of area is determined and used to calculate the elongation at zero, and the uniform elongation (elongation at infinite or distant location) is determined by the mode of the local elongation values determined at the gage markings.

Elongation as a function of Gage Length is determined from the distance data and the uniform elongation values determined above.

The Elongation as a function of Gage Length relationship derived from smaller (or larger) diameter specimens is scaled to reflect the elongation values as they would be generated on the standard 0.5 inch specimen.

Based on the scaled elongation as a function of gage length and the determined end point elongation values, a value for the material elongation that is representative of material properties can be calculated for use in FEA modeling the plastic behavior of a device.

DETAILED DESCRIPTION OF THE INVENTION

As used herein, "gage length" is defined as a marked length on a tensile test specimen over which strain, change of length and other characteristics are measured. The gage length can include the entire marked length or only a portion of the marked length. The term gage length will refer to the original gage length unless stated otherwise.

As used herein, "original gage length" is defined as the original marked length on a tensile test specimen prior to testing over which strain, change of length and other characteristics are measured.

As used herein, "final gage length" is defined as the marked length on a tensile test specimen after testing. Where the portion of the specimen measured includes a point of failure (i.e., a fracture), the final gage length measurements are taken after the specimen is fitted together at the fracture.

As used herein, "fracture zone" is defined as the region located symmetrically about the location on the specimen with the smallest diameter after testing (i.e., minimum diameter location). The fracture zone spans the distance between the farthest location of the fracture on both sides of the minimum diameter location. In the fracture zone, local elongation versus location does not take the same form as observed on the remainder of the specimen. To account for the difference, the gage lengths used for calculating elongation as a function of gage length are limited to values greater than or equal to the original fracture zone length.

As used herein the "original fracture zone length" is calculated from the final fracture zone length measured on the fractured specimen times (1 minus (% RoA divided by 100)) where the % RoA (i.e., reduction in area measured as a percentage of the original area) is the average of the % RoA at the minimum diameter and the % RoA at the furthest fracture location from the minimum diameter.

As used herein, "yield strength" is defined as the maximum stress (stress is generally understood to be the internal distribution of forces within a body) that can be developed in a material without causing plastic deformation. It is the stress at which a material exhibits permanent deformation and is a practical approximation of elastic limit.

As used herein, "ultimate tensile strength" (UTS) is defined as the highest engineering stress developed in a material before fracture. UTS is achieved at maximum load.

As used herein, "uniform strain" is defined as the plastic portion of the engineering strain occurring prior to the beginning of localization of strain (i.e., beginning of necking strain). In this invention, the uniform strain is measured and reported as uniform elongation, expressed as a percent of the original gage length.

As used herein, "necking strain" is defined as the plastic portion of the engineering strain occurring from the beginning of localization of strain to failure. In this invention, the necking strain is measured and reported as necking elongation, expressed as a percent of the original gage length.

As used herein, "residual engineering strain" is defined as the sum of the uniform strain plus the necking strain measured on the fractured specimen. Elastic strain is not included in this value. In this invention, the residual engineering strain is measured and reported as residual engineering elongation ("elongation"), expressed as a percent of the original gage length.

As used herein, "strain hardening rate" is defined as the rate of change of true stress as a function of true strain in a material undergoing plastic deformation. Strain hardening rate is also termed modulus of strain hardening.

As used herein, "tensile elongation to failure" ("elongation") is defined as the residual engineering elongation to failure, generally expressed as a percent of the original gage length measured on the fractured specimen.

As used herein, "local elongation" is defined as the elongation at a discrete location along the length of the tensile specimen. This value can be calculated from the change in specimen area at that location. Alternatively, local elongation can be approximated for the mid point between two gage markings using the elongation measured (based on distance) between the two gage markings.

As used herein "zero location" is the location of the minimum diameter after fracture. This is the reference point from which all locations are measured and on which all gage lengths are roughly centered.

As used herein, "elongation @zero" is defined as the calculated elongation of the specimen when the gage length is at or near zero length or the location is the zero location.

As used herein, "elongation at infinity or very long gage length" is defined as the uniform elongation. This is equivalent to the local elongation within the region(s) of uniform elongation on the failed specimen.

As used herein, "FEA" is defined as finite element analysis—a numerical method used to model device behavior under the stresses and strains anticipated in service.

FIG. 1 shows a tensile specimen 6. The specimen 6 includes a gripped region 14 on a first end 8 of the reduced region 10 and at a second gripped region 14 on a second end 9 of the reduced region 10. The gripped regions 14 can be any length, but are preferably about 4 times the specimen original diameter.

Figure 1A:
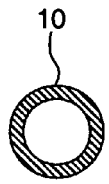
FIG. 1a is a cross section view of an embodiment of the specimen in FIG. 1.
Figure 1B:
FIG. 1b is a cross section view of an embodiment of the specimen in FIG. 1.

The specimen can be any material typically subject to tensile testing (e.g., ductile metals). Preferably, the specimen is solid (FIG. 1B) or tubular (FIG. 1A). Tubular specimens are typically made with the gripped regions having the same diameter as the original diameter. More preferably, the specimen is a solid or tubular cylindrical, substantially smooth tensile specimen. As used herein in describing the specimen, substantially smooth means unnotched or having isolated notches less than about 5% of the specimen section.

The method can include fabricating the specimen (as shown in FIG. 1). The fabricated solid specimen preferably has a reduced region 10, longer than that specified for proportional small size specimens in ASTM E8, Table 8.

The diameter of the reduced region 10 is preferably less than about 0.5 inch; more preferably, less than about ⅜ inch; and most preferably, from about 0.020 inch to about ⅜ inch.

The reduced region 10 is preferably at least 16, and more preferably 20 times, the original specimen diameter. This length is considerably longer than the minimum 4+ times diameter required by ASTM E8 table 8 for small size proportional specimens.

As shown in FIG. 1, the reduced region of the specimen 10 is marked with a pattern of gage markings 12 at predetermined regular intervals. The predetermined regular intervals can be, for example, about every 0.01 inch to about every 0.50 inch (e.g., every 0.125 inch), preferably approximately every 0.01 inch for every 0.04 inch of specimen reduced diameter. Alternatively, the regular interval can be defined in SI units. While regular intervals are preferred, non-identical intervals can be used on the same specimen. The pattern of markings can be the same for all small diameter specimens. The pattern of markings can be applied before or after the specimen is placed in the tensile tester. Preferably, the pattern of gage markings consists of a series of narrow lines applied with a durable ink.

In one embodiment of the present invention, the specimen 6 (as shown in FIG. 1) is placed in a tensile tester (not shown). The tensile tester secures the specimen 6 at a gripped region 14 on a first end 8 of the reduced region 10 and at a second gripped region 14 on a second end 9 of the reduced region 10. Tensile testers are known by those skilled in the art. Therefore, they need not be further described here.

The tensile specimen is pulled to failure in the tensile tester per the current ASTM E8 practice. Upon failure, the specimen breaks into two pieces at a fracture 18.

Specimen strain during tensile testing occurs in three distinct modes. At the onset of deformation, the specimen strains elastically, until yielding occurs. At this point, the specimen enters into the second mode of strain, where it strains plastically. At first, the plastic strain is uniformly distributed along the entire reduced region (so-called, uniform strain). Strain continues uniformly as long as the strain hardening rate is greater than the rate of the reduction in area. Under these conditions, strain occurs in localized areas causing the specimen to become hardened and consequently more difficult to strain in that local area. Further strain then occurs in another area of the specimen that is not as hard. Eventually, as the entire specimen becomes progressively harder and the strain hardening rate decreases, the reduction of area rate exceeds the strain hardening rate, a maximum load is achieved, and strain concentrates at one location. This concentration of strain (termed tensile instability or necking) is the third mode of strain and produces localized necking which ultimately leads to specimen failure. At failure, the elastic strain stored in the specimen is recovered when the tensile load is released.

Residual engineering strain to failure is the sum of the uniform strain plus the necking strain to failure measured on the fractured specimen. Because strain concentrates at the necked region in the final stages of failure, local strain in the necked region is greater than the uniform strain. In addition, the length of the necked region is proportional to the diameter of the specimen, so the length of the necked region reduces as the specimen diameter reduces. As a result, if the gage length is fixed (e.g., 2 inches), the necked region represents a smaller portion of the gage length for specimens with smaller diameter. This leads to measured elongation values for small diameter (e.g., less than 0.5 inch) specimens that are lower than the values for larger diameter specimens of similar material with similar material properties.

The present invention addresses the specimen size effect by creating elongation measures at or near zero and at infinite or very long gage lengths that are independent of gage length. In addition, the Elongation as a function of Gage Length relationship derived from smaller (or larger) diameter specimens is scaled to reflect the elongation values as they would be generated on the standard 0.5 inch specimen.

After testing, the specimen is removed from the tensile tester. The two pieces of the specimen are fitted together at the fracture 18 per current practice. Fitting together of the pieces is known by those skilled in the art, and therefore will not be discussed in detail here. The specimen is then fixed in place on a holder.

Figure 2:
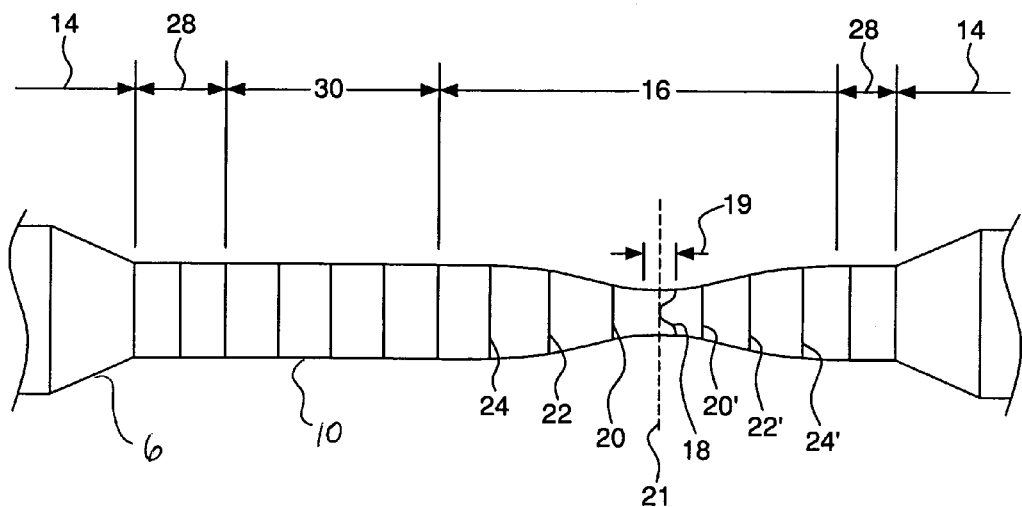
FIG. 2 is a plan view of the tensile specimen of FIG. 1 after tensile testing.

FIG. 2 shows the specimen (as shown in FIG. 1) 6 after it has been tested and fitted together. The fractured specimen still includes the reduced region 10 the gage markings 12 and the gripped regions 14. After testing, the specimen also includes two regions adjacent to the gripped regions with reduced elongation because they are closer to the gripped region (the so-called end effect regions 28), a uniformly elongated region 30, a necked region 16, a fracture zone 19, a minimum diameter location 21 and the fracture 18. The fracture 18 is the point of failure from the testing. The fracture zone 19 is the area of the specimen encompassing the entire fracture 18. The minimum diameter location 21 is the location on the specimen having the smallest diameter after testing. The uniformly elongated area 30 is the area where the specimen is subject to uniform strain. More than one uniformly elongated area 30 can be present on the specimen. The necked region 16 is the area where the specimen is subject to necking strain.

After the specimen is fitted together at the fracture, final gage lengths are measured. In this embodiment, the final gage lengths are the distance between two corresponding gage length markings, one on each side of the fracture. The final gage length for the first set of markings 20, 20' nearest the fracture is measured first. Subsequently, final gage lengths for additional sets of markings are measured. The subsequent sets of markings extend progressively outward from the fracture to the second 22, 22', third 24, 24', and up to the $20^{th}$ set of markings straddling the fracture. Although it is preferred that the first set of markings is measured first, the present invention is not so limited.

Using the measured final gage lengths, elongation as a function of original gage length is calculated for each set of markings with the following formula: Percent Elongation= [(Final gage length of $n^{th}$ set of markings minus original gage length of $n^{th}$ set of markings) divided by original gage length of $n^{th}$ set of markings] times 100; wherein n represents the number of markings from the fracture (e.g., n=1 for the set of markings that includes the first markings on either side of the fracture). This formula is used for each set of markings and the percent elongation values are recorded along with the original gage length, preferably in a spreadsheet.

Figure 5:
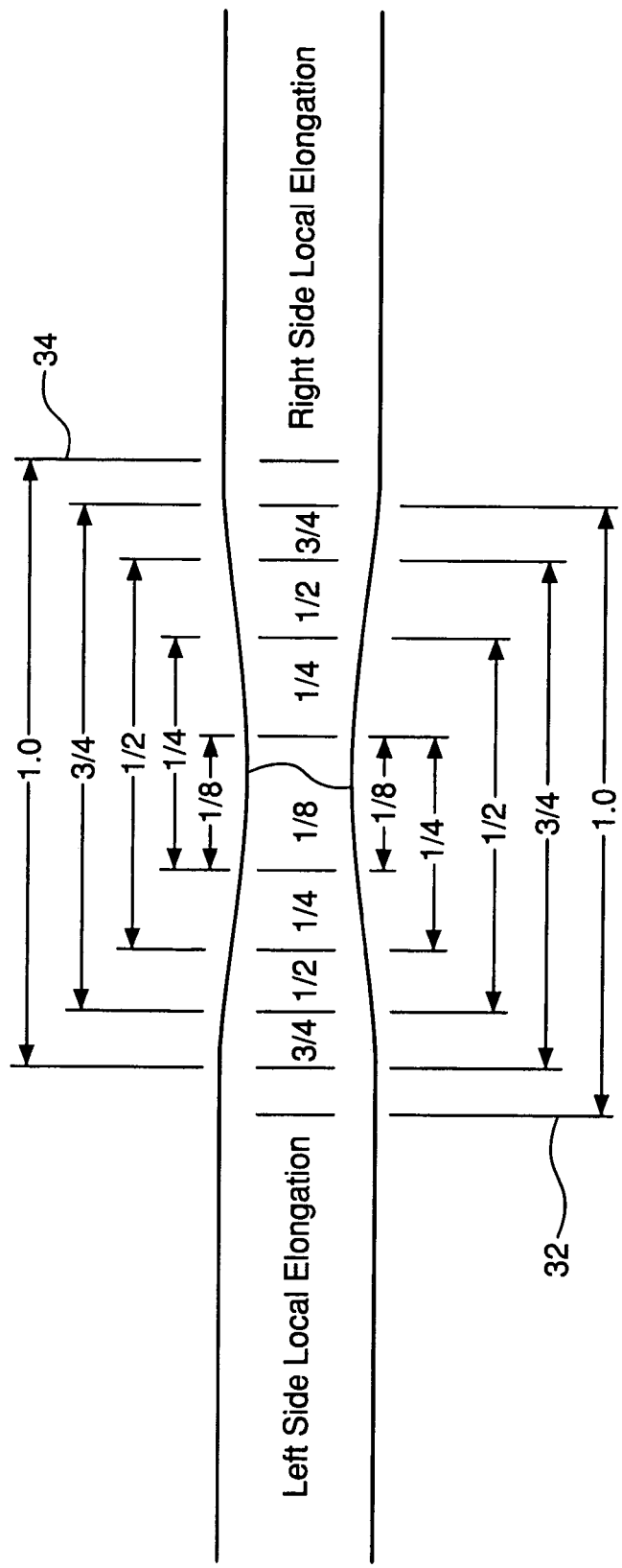
FIG. 5 is a plan view of the tensile specimen after tensile testing in which left and right elongation values are used to produce an average elongation which corrects for the fact that the fracture is almost never located half way between two gage markings.

In an alternate embodiment of the invention, the final gage lengths for all but the first set of gage markings are measured using the left gage lengths 32 and the right gage lengths 34 shown in FIG. 5. The final gage lengths are measured in the same manner as described above except that the left and right final gage lengths are measured independently. The resultant elongation values are then averaged. The average elongation thus calculated for each gage length corrects for the fact that the fracture (or minimum diameter) is almost never located exactly at the midpoint between the first pair of markings.

The final diameters of the specimen are also measured after testing. The final diameters are measured at the location on the specimen having the smallest diameter (i.e., the so-called minimum diameter, which is adjacent to the fracture), at the fracture location furthest from the minimum diameter location, and at each of the gage markings. These final diameter measurements can be compared with the original diameter of the specimen to determine the local reduction in area at each measured location. The final diameters can also be used to calculate local elongations in place of, or in addition to, the final gage length measurements using the equation, Local Elongation/100=1/(1−local % RoA/100)−1, where local % RoA is the local reduction in area measured as a percentage using the following equation: % RoA=100×(Original Diameter^2−Final Diameter^2)/ Original Diameter^2).

The uniform elongation is determined by finding the statistical mode of all the local elongation values. The mode is not affected by the lower elongations of the end effect regions which would be included in the E8 method. The mode is also not effected by the necking region on the specimen pulled to failure. The mode can be determined from all local elongation data from an individual specimen or, alternatively, based on local elongation data from a number of specimens.

Figure 3:
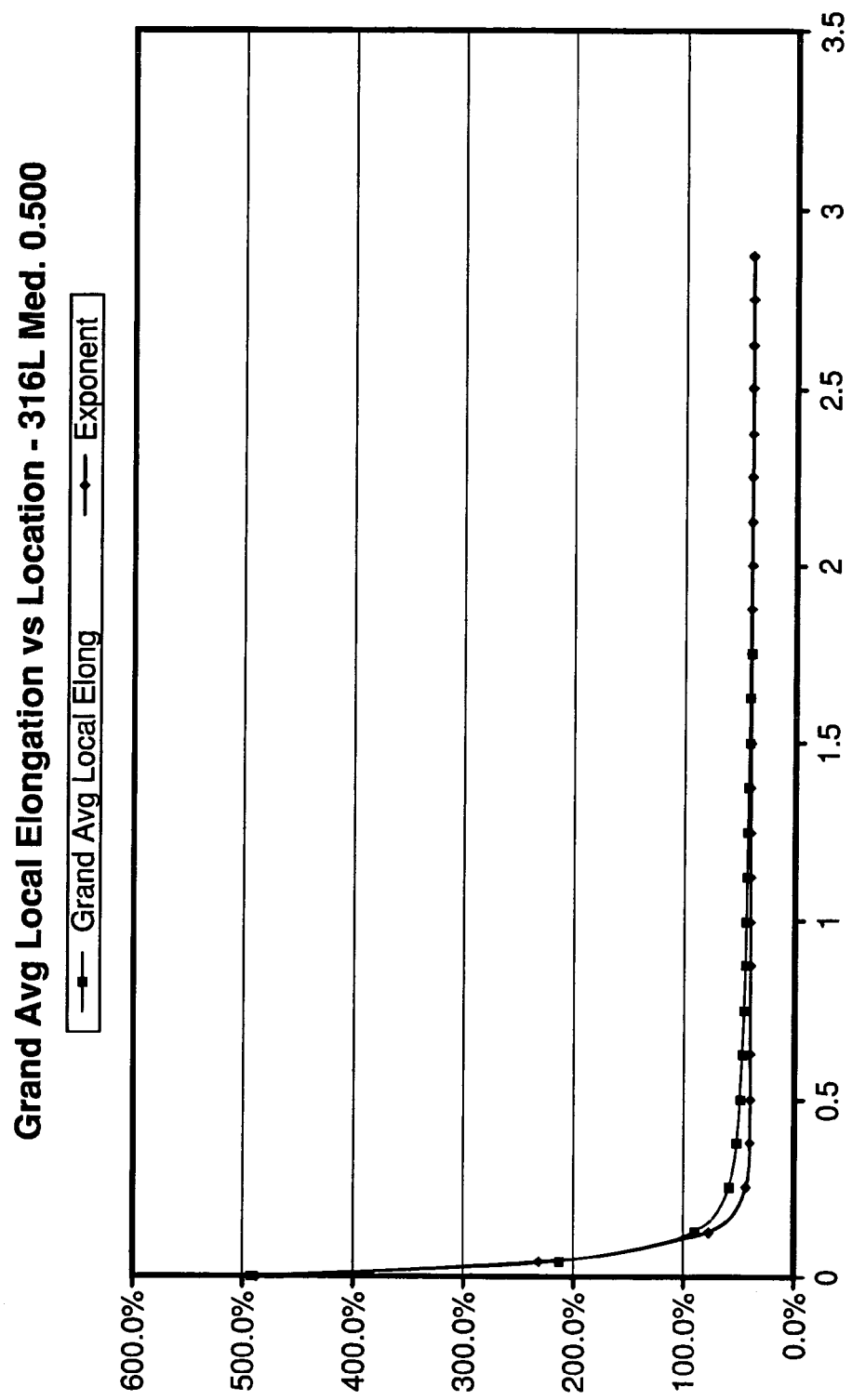
FIG. 3 is a graph of the grand average local elongation versus location derived from a number of fractured specimens using the present invention. The exponential trend line presented as a part of this invention is also shown.

The distances, locations, and diameters from the gripped regions and the end effect regions are discarded. The percent local elongation calculated at the minimum diameter and each gage marking is then graphed versus location (distance from the minimum diameter location). FIG. 3 is an example of such a graph. FIG. 3 shows the grand average local elongation graphed versus location for thirty 0.5 inch diameter 316LVM tensile specimens. Local elongation is defined above. The values for FIG. 3 were calculated from original and final diameters. Location is the original distance on the tensile specimen from the minimum diameter location. This data was generated using the method defined below. The original location is determined by the gage markings. The Y intercept (just under 500%) is the grand average local elongation @zero (minimum diameter) location calculated from the % RoA. The local elongation drops quickly in the necked region adjacent to the minimum diameter, approaching the asymptote value of ~40% (equal to the uniform elongation) at about the 1 inch location. The "exponential" equation detailed below and used to model the determined data is also shown.

A best fit exponent curve is generated for local elongation versus distance having the following formula: Y=(b−a)(e^−c*X)+a, where Y is the calculated local elongation, X is the distance from the minimum diameter location, a is the asymptote value (which represents uniform elongation), b is the y intercept (which represents elongation @zero).

Uniform elongation and the elongation @zero are independent of gage length. These values can be determined by using experimental data to represent the calculated elongation to failure ("Y") and the location ("X") in the following equation: $Y=(b-a)(e^{-c*X})+a$. Experimental data can also be used to represent uniform elongation. Alternatively, uniform elongation and elongation @zero can be solved for using the experimental data to represent the other parameters and by setting X to infinity for uniform elongation and by setting X to zero for elongation @zero.

Elongation @zero minus uniform elongation (b-a) is defined as the "necking elongation @zero". This value is independent of gage length.

Necking Elongation @zero times $(e^{-c*X})$ is the contribution of necking elongation to total elongation at any particular distance from the minimum diameter. Adding this product to the uniform elongation ("a") produces a curve (FIG. 3) that defines the variation of local elongation with location (distance from the minimum diameter).

The method of the present invention can also be used to calculate reduction of area of a specimen with a solid section. Elongation @zero by the method is analogous to the reduction of area (% RoA) reported for solid specimens in that both are measured at the minimum diameter and are independent of gage length. Using the concept of conservation of volume, these measures of elongation have been shown by others to be related mathematically for solid specimens as follows: % RoA/100=1−(1/(1+Elongation @zero/100)). Alternatively, the following equation relates the elongation at zero gage length with the reduction of area:

Elongation @zero/100=(1/(1−% RoA/100))−1.

Original Fracture Zone length is calculated using two times the distance between the location of the minimum diameter and the furthest location of the fracture times (1 minus Local % RoA/100) where the Local % RoA is the average of the local % RoA at the minimum diameter and the local % RoA at the fracture.

A local elongation versus location curve can be graphed to determine if the derived end point values and data appear to produce a continuous relationship according to the following "exponential" equation:

Local Elongation=(Necking Elongation @zero)($e^{-C*Location}$)+Uniform Elongation where Location is the distance from the minimum diameter location.

Elongation as a function of gage length is then determined using the location measurements and the resulting final distance between gage markings, the Uniform Elongation, and the Original Fracture Zone length in the following "inverse power" equation:

Elongation=((Necking Elongation @GL=1)(Gage Length)$^{-Exponent}$)+Uniform Elongation where the Gage Length is greater than or equal to the original Fracture Zone length.

The Elongation as a function of Gage Length relationship derived from smaller (or larger) diameter specimens is scaled to reflect the elongation values as they would be generated on the standard 0.5 inch specimen using the "scaled inverse power" equation having the form:

Elongation=((Necking Elongation @GL=1)(((2*Diameter)^0.5) Gage Length)$^{-Exponent}$)+Uniform Elongation where the Gage Length is greater than or equal to the original Fracture Zone length and the Diameter and the Exponent may vary with material or other factors.

The values of the Necking Elongation @GL=1 and the exponent are determined by graphing Elongation versus Gage Length data and generating the best fit equation using the power trend line function in a graphics analysis program.

Elongation @zero (or near zero) can be determined using the above equation and setting the Gage Length equal to the Original Fracture Zone length. This calculation solves for the elongation at the end of the fracture zone.

These equations can be generated using data from a single specimen or the average of data from a number of specimens.

In order to permit curve fitting (to determine the value of necking elongation @GL=1 and the Exponent), the uniform elongation may have to be subtracted from the total elongation at each gage length. The resulting Necking Elongation is graphed versus the Gage Length and a power trend line is generated to fit the data.

The Uniform Elongation is then added to the necking elongation equation to produce the equation for Elongation as a function of Gage Length.

The process for determining the Elongation as a function of Gage Length is modified for tubular sections using the mathematical relationship that true mid-wall diametral strain plus true wall strain equal total true strain.

Figure 4:
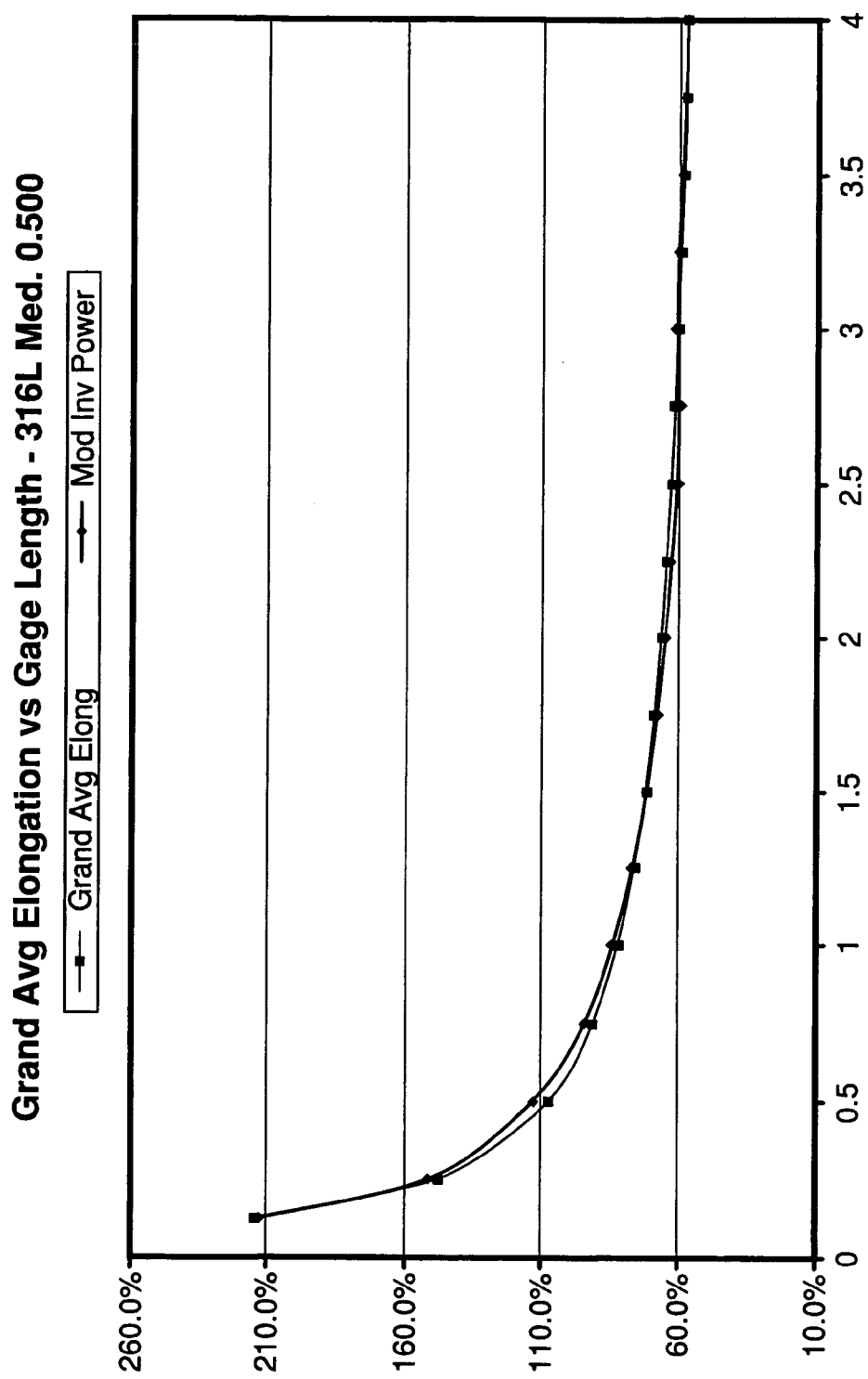
FIG. 4 is a graph of the grand average elongation versus gage length derived from a number of fractured specimens using the present invention. The inverse power trend line presented as a part of this invention is also shown.

From the Elongation as a function of Gage Length equation an elongation value can be determined that models a tensile specimen having any diameter and any particular gage length. For example, as shown in FIG. 4, a 0.500 inch specimen with a gage length of 2 inches would have an elongation of about 66%. FIG. 4 shows the grand average elongation graphed versus gage length for thirty 0.5 inch diameter tensile specimens. The elongation is calculated using the change in gage length method described above. Gage length on the x axis is the original gage lengths marked on the specimen before testing. Since the elongation is inversely related to gage length, there is no Y intercept on this graph. Instead of a zero gage length, the fracture zone length is used to define the minimum gage length (near zero gage length) for which this method and graph can be used. The first value shown is the grand average elongation (~215%) at the first gage marking (0.125 inch). The elongation does not drop as quickly here as the local elongation vs. location graph (FIG. 3) due to the rolling average effect that occurs when elongation is calculated at progressively longer gage lengths. Using this method each progressively longer gage length includes the extremely high elongation of the fracture. The elongation drops to approximately 75% at 1 inch (GL=1). The elongation does not approach the asymptote value (~40%) equal to the uniform elongation until the gage length exceeds 4 inches. The scaled inverse power equation detailed in 75 above and used to model the data is also shown.

Based on the determined elongation as a function of gage length and the determined end point elongation values, a value of elongation that is representative of material properties can be generated for use in prediction of device plastic behavior in FEA modeling.

Elongation values that are appropriate in FEA modeling generally range from the uniform elongation (very conservative) to the elongation at or near zero gage length (very aggressive) or more preferably some intermediate value. The choice of uniform elongation is quite conservative since plastic deformation up to the point of maximum load is predictable and uniform throughout the specimen. The choice of the elongation at or near zero gage length would be very aggressive due to the extreme localization of the strain due to necking, the presence of a triaxial stress state in the specimen, and the onset of fracture at this value. An intermediate value would be more appropriate in predicting plastic behavior of a device.

For devices operating in a controlled stress environment (i.e., a specific load is applied to the device by an external source) aggressive elongation choices beyond the uniform elongation are inappropriate. In this environment, if the maximum load (i.e., end of uniform strain) is reached, strain will progress rapidly at reducing load to failure.

For devices operating in a controlled strain environment (i.e., a specific strain is applied to the device by an external source), more aggressive elongation values are appropriate. In this type of environment, the device will strain to accommodate the externally applied strain until either fracture occurs or the strain from the external source reaches the strain controlled limit. Balloon expansion of a stent is closer to a strain controlled environment than a stress controlled environment.

In an alternate embodiment of the invention, the step of measuring the multiple sets of gage markings straddling the fracture and the step of measuring the set of markings furthest apart (which also straddle the fracture) are replaced. In place of these steps, the specimen is measured on a non-contact measuring device (e.g., an optical micrometer) starting from the first marking outside the gripped region on one end. From that marking, the location of each subsequent gage marking is measured until the fracture is reached, at which point the location of the fracture and the minimum diameter are measured. The remaining gage marking locations including the last marking prior to the gripped region are then measured. These measurements are termed unilateral final gage lengths. The percent elongation is calculated for each measurement based on the following formula: Percent elongation=[(Unilateral final gage length−original gage length)/(original gage length)]*100. Once the elongations are calculated, the remaining steps of the embodiment are substantially similar to the previous embodiment.

In an alternate embodiment of the invention, the final gage marking locations and diameters at the prescribed locations are measured at one time from one end of the specimen. This may be done manually using an X Y measuring microscope, or automatically using a 2 axis vision system. Use of a 2 axis vision system allows the measurement of location and diameter simultaneously as well as entering the data electronically into the calculating spreadsheet. The spreadsheet is programmed to calculate the Percent Elongation at each gage mark and for each progressively longer gage length from distance and/or diameter as described above.

In an alternate embodiment of the invention all elongation values are expressed as true strains, and calculations are performed using true strains. According to this embodiment, true strain is related to gage length using the following "true strain inverse power" equation:

$$\text{True Strain} = (\text{True Strain } @GL=1)(\text{Gage Length}^{-\text{Exponent}})$$

where Gage Length is greater than or equal to the original Fracture Zone length.

It will be appreciated by those skilled in the art that the present invention can be practiced in various alternate forms and configurations. The previously detailed description of the disclosed methods is presented for clarity of understanding only, and no unnecessary limitations should be implied therefrom.

What is claimed is:

1. A method for measuring and calculating elongation to failure on a tensile specimen, the method comprising:
   providing a tensile specimen having gage markings at predetermined intervals;
   tensile testing the specimen to failure, the specimen after failure having a fracture;
   measuring locations of the gage markings and fracture relative to a minimum diameter, the minimum diameter comprising a location on the specimen having the smallest diameter;
   measuring diameters of the specimen at the gage markings, the fracture and the minimum diameter;
   determining local elongation as a function of location on the specimen;
   determining end point elongation values at zero and at infinite locations; and
   determining from the elongation and end point elongation values a value of elongation for modeling plastic deformation of a device made of the same material as the specimen.

2. A method for measuring and calculating elongation to failure on a tensile specimen having an original reduced region and an original diameter, the method comprising:
   marking the tensile specimen with a pattern of gage markings at predetermined intervals;
   testing the tensile specimen by holding the tensile specimen at gripped regions and pulling the tensile specimen to failure, the specimen after testing having two end effect regions adjacent to the gripped regions, a uniformly elongated region, a necked region, a minimum diameter, a fracture at least partially between two markings, the two markings forming a first set of gage markings straddling the fracture, and a fracture zone totally encompassing the fracture;
   fitting the tensile specimen together at the fracture;
   measuring a first final gage length, the first final gage length comprising a distance between the first set of markings straddling the fracture;
   repeating the measuring of final gage lengths for additional sets of markings straddling the fracture, the additional sets extending progressively outward from the fracture;
   measuring locations, relative to the minimum diameter, of the gage markings and the fracture;
   measuring final diameters of the tensile specimen at the gage markings, at the minimum diameter and at the fracture;
   discarding the locations and diameters from the end effect regions;
   determining end point elongation values, the end point elongation values comprising elongation at zero or near zero and infinite or very long gage lengths, the elongation value at infinite or very long gage length comprising uniform elongation;
   determining elongation as a function of gage length for each set of gage markings;
   scaling the elongation as a function of gage length relationship to reflect elongation values as they would be generated on a standard 0.5 inch specimen; and
   determining from the scaled elongation as a function of gage length and the determined end point elongation values, a value of elongation for finite element analysis modeling plastic deformation behavior of a device made of the same material as the specimen.

3. A method according to claim 2, wherein the original diameter is less than about 0.5 inch.

4. A method according to claim 3, wherein the original diameter is less than about 0.375 inch.

5. A method according to claim 2, wherein the original reduced region is at least 16 times the original diameter.

6. A method according to claim 5, wherein the original reduced region of at least 20 times the original diameter.

7. A method according to claim 2, wherein the tensile specimen has a solid section.

8. A method according to claim 2, wherein the tensile specimen has a tubular section.

9. A method according to claim 2, wherein the pattern of gage markings consists of a series of narrow, durable lines.

10. A method according to claim 2, wherein the predetermined interval is approximately 0.01 inch for each 0.04 inch of the original diameter of the specimen.

11. A method according to claim 2, wherein the predetermined interval is about 0.125 inch.

12. A method according to claim 2, wherein determining elongation as a function of gage length for each set of markings comprises:

calculating a percent elongation between sets of markings using the following formula:

[(final gage length of the $n^{th}$ set of markings−original length of the $n^{th}$ set of markings)/original gage length]*100, wherein n represents the number of markings from the fracture, the final gage length comprising the length between the $n^{th}$ set of markings after testing and the original gage length comprising the length between the $n^{th}$ set of markings before testing; and repeating the calculation for each set of gage markings.

13. A method according to claim 2, further comprising:

determining local elongation at each gage marking, at the minimum diameter, and at the fracture; and determining the uniform elongation by finding the statistical mode of all the local elongation values of the specimen.

14. A method according to claim 13, further comprising determining an Original Fracture Zone length from the following equation:

Original Fracture Zone length=2*(distance from the minimum diameter to a location of the fracture farthest from the minimum diameter)*(1−(local % RoA/100 at the minimum diameter+local % RoA/100 at the fracture)/2).

15. A method according to claim 14, wherein determining the Elongation @zero or near zero gage length comprises solving for Elongation in the following formula when Gage Length is greater than or equal to the Original Fracture Zone length:

Elongation @zero=((Necking Elongation @GL=1)(Gage Length)^−Exponent)+Uniform Elongation wherein Necking Elongation @GL=1 and the Exponent are determined by using a best fit power equation generated from the determined elongation values and the measured gage lengths.

16. A method according to claim 15, wherein the Gage Length is equal to the Original Fracture Zone length.

17. A method according to claim 2, wherein the scaling is performed using an equation having the form:

Elongation=((Necking Elongation @GL=1)(((2*Diameter)^0.5) Gage Length)^−Exponent)+Uniform Elongation, where the Gage Length is greater than or equal to the original Fracture Zone length.

18. A method according to claim 2, wherein all values are expressed as true strains and all calculations are done using true strains, and wherein the following equation relates true strain to gage length:

True Strain=(True Strain @GL=1 (Gage Length^−Exponent)

where Gage Length is greater than or equal to the original Fracture Zone length.

19. A method according to claim 2, wherein the value of elongation to model the plastic deformation behavior of the device comprises:

calculating percent elongation for each set of gage markings, calculating necking elongation by subtracting the uniform elongation from the percent elongation;

plotting the necking elongation versus the original gage length for each set of markings;

generating a best fit power curve and equation for necking elongation versus gage length;

determining a mathematical relationship relating necking elongation and gage length from the equation of the best fit power curve, adding the uniform elongation to the necking elongation values to create an elongation versus gage length equation: Elongation=((Necking Elongation @GL=1.) *Gage Length)^−Exponent)+Uniform Elongation;

scaling the Elongation as a function of Gage Length relationship to reflect elongation values as they would be generated on a standard 0.5 inch specimen; and applying a gage length based on a level of necking elongation that can be tolerated by the device to produce an elongation value to be used for FEA modeling of device plastic behavior.

20. A method for measuring and calculating elongation on a tensile specimen, the method comprising:

marking the tensile specimen with a pattern of markings at predetermined intervals;

placing the tensile specimen in a testing device, the testing device securing the tensile specimen at gripped regions of the specimen testing the tensile specimen by pulling the tensile specimen to failure, the specimen after testing having gripped regions, two end effect regions adjacent to the gripped regions, a region with uniform elongation, a necked region, a minimum diameter, a fracture at least partially between two markings, and a fracture region adjacent to the fracture, fitting the tensile specimen together at the fracture;

measuring gage markings from one end of the specimen and calculating the final gage lengths from the measurements;

measuring diameters after testing of the tensile specimen at the gage markings, at the minimum diameter, and at the fracture;

determining local elongation at each gage marking, at the minimum diameter and at the fracture, determining uniform elongation from the mode of all the local elongation values;

determining elongation as a function of gage length for each set of markings;

determining end point elongation values, the end point elongation values comprising elongation at zero and infinite gage lengths;

scaling the elongation as a function of gage length relationship to reflect elongation values as they would be generated on a standard 0.5 inch specimen; and determining a value of elongation to model plastic performance of a device from the scaled elongation as a function of gage length and the determined end point elongation values.

* * * * *